United States Patent [19]

Feickert et al.

[11] Patent Number: 4,865,998

[45] Date of Patent: Sep. 12, 1989

[54] MONOCLONAL ANTIBODIES TO HUMAN LUNG CANCERS AND METHOD

[75] Inventors: Hans-Joachim Feickert; Wolfgang Rettig; Karen Chorney; Carlos Cordon-Cardo, all of New York; Myron R. Melamed, Scarsdale; Kenneth O. Lloyd, Bronx, all of N.Y.; Herbert F. Oettgen, New Canaan, Conn.; Lloyd J. Old, New York, N.Y.; Bernd Anger, Ulm, Fed. Rep. of Germany

[73] Assignee: Sloan-Kettering Institute for Cancer Research, New York, N.Y.

[21] Appl. No.: 83,723

[22] Filed: Aug. 10, 1987

Related U.S. Application Data

[63] Continuation of Ser. No. 474,225, Mar. 11, 1983, abandoned.

[51] Int. Cl.$^4$ ............... G01N 33/574; G01N 33/577; C12N 5/00
[52] U.S. Cl. ............................. 436/548; 435/240.27; 435/948; 935/104
[58] Field of Search .................. 435/7, 68, 172.2, 240, 435/27, 948; 436/548; 935/104

[56] References Cited

PUBLICATIONS

Mazauric et al., Cancer Research 42, pp. 150–154 (1982).
Kasai et al., Journal of Surgical Research 30, pp. 403–408 (1981).
Kasai et al., Transplantation Proceedings, vol. XIII (4), pp. 1942–1946 (1981).
Cuttitta et al., Proc. Natl. Acad. Sci. 78(7), pp. 4591–4595 (1981).
Minna et al., In Vitro 17(12), pp. 1058–1070 (1981).
Anger et al., Hybridoma 1(2), pp. 139–147 (1982).
Stepelewski et al., Federation Proceedings 40(3), p. 823, Abstract #3369.

Primary Examiner—John E. Tarcza
Attorney, Agent, or Firm—John P. White

[57] ABSTRACT

A panel of monoclonal antibodies produced from normal human lung fibroblasts and human lung tumors as immunogen is used to diagnose the presence of lung tumors and differentiate between those which are benign and those which are cancerous.

4 Claims, No Drawings

MONOCLONAL ANTIBODIES TO HUMAN LUNG CANCERS AND METHOD

This invention was made in part with government support under Grant No. CA 08748 awarded by The National Cancer Institute. The government has certain rights in this invention.

This is a continuation of application Ser. No. 474,225, filed Mar. 11, 1983.

BACKGROUND

This invention concerns monoclonal antibodies recognizing human lung cells. The monoclonal antibodies recognize antigenic markers on normal as well as cancerous lung cells. Capable of distinguishing normal lung versus cancerous lung tissues, these mAbs are useful in diagnosis of lung cancer. Tests with these mAbs also enable diagnostic differentiation between benign tumors versus cancerous tumors of the lung.

In 1975 Köhler and Milstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Kohler-Milstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361-375, February 1981) The analysis of these T-cell differentiation antigens was greatly simplified by the availability of normal T cells and B cells of mouse and man and is relatively advanced. (See Pat. Nos. 4,361,549-550; 4,364,932-37 and 4,363,799 concerning mAb to Human T-cell antigens).

Little is known about differentiation antigens displayed on normal and neoplastic cells belonging to other lineages.

This is due to the difficulty of obtaining a ready source of the appropriate normal cell type as well as the vagaries of the art of monoclonal antibodies. The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad, Sci. USA, 79 2018 (March 1982). This method provides a renewable source of proliferating cells for the analysis of melanocyte differentiation antigens. Likewise, a large number of cell lines derived from melanomas have now been established and these have facilitated the analysis of melanoma surface antigens. The advent of mAb has greatly accelerated knowledge about the surface antigens of malignant melanoma. Cell markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. Dippold et al. *Proc. Nat'l. Acad. Sci. U.S.A.* 77, 6114 (1980) and Houghton, et al. *J. Exp. Med.* 156, 1755 (1982). Immunoassay of melanocytes and melanoma cells within sub-sets in thus made possible.

SUMMARY

Assays for distinctions between normal lung, benign lung tumors, and lung cancer tissues are important diagnostic tools for clinicians and surgeons.

Cytohistological methods to date are not always successful. A panel group consisting maximally of seventeen mAbs of the present invention recognizing cancerous lung cells enables such a distinction for the first time. In addition, the panel distinguishes normal from cancerous cells.

The invention thus comprises hybridoma cell line producing mAbs recognizing human lung cancer cells from the group of F-1, F-2, F-3, F-4, F-5, F-7, F-8, F-9, F-10, F-11, F-12, F-13, F-15, F-16, F-17, F-18, F-19 mAbs of the invention which recognize lung antigens having a molecular weight in the range of approximately 30-180 kd (kilodaltons). The antigens are either heat stable glycolipids or heat labile glycoproteins. Antibody F-7 recognizes a 48 and 180 kd glycoprotein. $F_{15}$ recognizes a 44 kd glycoprotein.

DESCRIPTION

A preferred embodiment of the present invention is to test cells of a patient with each of the monoclonal antibodies of the panel. The cells are tested or contacted separately with each of the monoclonal antibodies in series dilution. Thus, an assay for cancer is possible with minimal patient disruption. Use of body fluids and exudates is preferable. Indeed, the present invention permits testing of human specimens for cell fragments containing antigenic markers for the monoclonal antibodies. Thus markers shed into the sputum can be tested as well.

The monoclonal antibodies of the present invention were prepared by an improved Kohler-Milstein procedure wherein spleen cells from a mouse (or other mammal) immunized with normal human or cancerous human lung cells are fused with mouse myeloma ns/1 to form hybridomas. By serological screening, antibodies from these hybridomas are found which recognize differentiation antigens on normal lung and/or cancerous lung. Other tissues, both normal and cancerous, may be recognized as well by some of these monoclonal antibodies. Benign tumors may be distinguished from cancerous tumors of the lung. A system of classification of normal as well as cancerous lung based on these differentiation antigens is now possible, and serological assays for tumors of the lung using monoclonal antibodies to these markers has been developed.

The assay of the present invention comprises contacting a tissue or sputum sample containing lung cells or antigenic components thereof with the antibody recognizing lung cell antigens, preferably monoclonal antibodies to one or more cell antigens of the lung antigenic system, and observing the immunoserological or immunopathological antigenic reaction between said monoclonal antibody and said antigen. In a preferred embodiment of the invention, the tissue sample to be contacted is lung tissue and the antigenic reaction to the contacted tissue is observed by well known techniques such as immunofluorescence, radioactive mAb, rosette formation with sheep or human red blood cells linked to Protein A or to anti-immunoglobulin, direct absorption and the like.

In another preferred embodiment of the invention unknown human cell specimens are analyzed for mAb reaction with each member of the cell panel using cell sorters for flow cytometry. Thus, the number of cells reacting with fluorescent mAb can be counted. The other well-known observation techniques can be employed to count the number of cells expressing the mAb antigen. In another embodiment of the present invention, the tissue to be assayed is first excised and is then either freshly, or after being frozen or embedded in paraffin by methods well-known in the art, contacted with the monoclonal antibodies of the invention. Observation of the reaction is as before, for example, using immunoflourescence or peroxidase.

In another preferred embodiment of the present invention, the tissue to be assayed comprises the intact body of an individual or a whole portion thereof. The antibody, tagged with a radioactive or other energy-producing element, is administered to the individual, and the whole body or part thereof is scanned externally for localization of radioactivity at the site of cancerous urothelial cells.

The present invention also makes possible the treatment of lung tumors in a patient wherein the monoclonal antibody recognizing the cell antigen of cancerous transitional epithelial cells, preferably the cell differentiation antigen, is administered to the patient in an amount effective to inhibit the growth or proliferation of cancer cells. In a preferred embodiment of this method, the antibody is tagged with a potentially tissue destructive agent which causes destruction of the cancer cells within the patient. Examples of tissue destructive agents comprise chemotoxic agents, chemotherapeutic agents including vaccines, radionuclides, toxins, complement activators clotting activators and the like.

The above examples are for illustrative purposes only and are not meant to limit the scope of the invention.

Examples of Antibodies, and Antigens Recognized

The following examples are intended to illustrate the invention without limiting same in any manner especially with respect to substantially functional equivalents of hybridomas, monoclonal antibodies and cell lines described and claimed herein which equivalents can be produced in accordance with the invention following the procedures outlined in the specification of this application.

The monoclonal antibodies selected for use in the present invention were derived from spleen cells of mice immunized with normal lung fibroblast cells (from fibroblast line C.A.), or the following lung tumors: epidermoid lung carcinoma (SK-LC-8), anaplastic large cell lung carcinoma (SK-LC-6) or mixed adeno- and oat cell (small cell) (SK-LC-2) carcinoma. Fusion methods well known in the art between mouse myeloma and spleen cells are done.

SK-LC-2 leads to the production of clones which give mAbs F-8, F-9, F-10, F-11 and F-12. SK-LC-6 produces clones which give mAbs F-1, F-2, F-4, F-5, F-7, and F-13. SK-LC-8 leads to the production of clones which give mAbs F-15, F-16, F-17 and F-18. Normal lung fibroblast cells lead to the production of clones which give mAb F-19.

A group of monoclonal antibodies, found to recognize specific cell antigens of lung cells, is selected as the lung panel. This panel and the antigenic systems recognized are given in Tables I-V. Heterogeneity of human lung carcinoma is therein noted. The table data point out and define the heterogeneity of lung carcinomas. A number of distinct new antigenic systems of lung cancer are defined by these mAbs as determined by serological analysis with 22 NSCL cell lines, other tumor lines and normal human cell lines (Tables I & II). Fifteen mAbs showing different patterns of reactivity in initial screening are tested serologically in this manner. Mixed hemadsorption and absorption analyses indicate three categories of reactivity with cultured cells: (1) restriction to NSCL; (2) reactivity with NSCL and other cancer types; (3) reactivity with cancer as well as normal cell types (other mAbs). These results using cultured cells are summarized in Table III and are compared with immunopathology done on frozen sections of normal adult and normal fetal tissue (Table IV). Table V shows reaction of some of these lung mAbs with frozen sections of tumors. mAbs F-1, F-2 and F-4 showed reactivity with a proportion of NSCL and other cancers but not with any normal tissue tested. Some mAbs reacted with distinct subsets of NSCL and also with a range of normal and other malignant tissues. F-5 distinguishes benign and malignant lung. F-5 also detects normal lung epithelium as shown on Table IV. mAbs F-7, F-8, F-10, F-15, F-16, F-17, F-18, F-19 are gamma sub one (gamma$_1$) immunoglobulines (Ig). F-11 is a gamma Sub 2B (gamma$_{2B}$) Ig and F-1, F-2, F-3, F-5, F-12, F-13 and F-4 are M globulins. F-7 and F-18 antigen are heat labile suggesting glycoprotein.

Changes in cell antigens are associated with different stages of differentiation. Thus, this invention technique defines cell antigens associated with lung cancer.

The following hybridoma lines are maintained on deposit at Sloan-kettering Institute for Cancer Research, 1275 York Avenue, New York, N.Y. 10021 under designations corresponding to the mAb produced by each hybridoma as follows: F-1, F-2, F-3, F-4, F-5, F-7, F-8, F-9, F-10, F-11, F-12, F-13, F-15, F-16, F-17. These mAbs are also known as lung mAbs S-1, S-2, S-3, S-4, S-5, S-6, S-7, S-8, S-9, S-10, S-11, S-12, S-13, S-15, S-16, S-17, S-18, S-19 when supernatant fluid from hybridoma cell line cultured is used for testing. Said hybridoma lines have been deposited with the American Type Culture Collection, 1230 Parklawn Drive, Rockville, Md. 20852 under ATCC designations corresponding to the above Sloan-Kettering designations.

Deposit date: March 11, 1983

| Sloan-Kettering deposit | Corresponding ATCC deposit/ Accession # |
|---|---|
| F-10 | HB 8261 |
| F-11 | HB 8262 |
| F-12 | HB 8263 |
| F-13 | HB 8264 |
| F-15 | HB 8265 |
| F-16 | HB 8266 |
| F-17 | HB 8267 |
| F-18 | HB 8268 |
| F-19 | HB 8269 |
| F-1 | HB 8230 |
| F-2 | HB 8253 |
| F-3 | HB 8254 |
| F-4 | HB 8255 |
| F-5 | HB 8256 |
| F-7 | HB 8258 |
| F-8 | HB 8259 |
| F-9 | HB 8260 |

Legend to Table 1

Serological reaction of lung panel monoclonal antibodies with tumor cell lines of various tissues by rosette formation with human red blood cells conjugated with rabbit anti-mouse Ig (Dippold et al, Supra) where 0=no reaction 2=reaction at <10,000 fold dilution antibody supernatant 3=reaction at >10,000 fold dilution antibody supernatant If there was no reaction by the above test, the absorption test was done, except no absorption test was done for F-8, F-10, F-11, F-1, F-2, F-3, F-5, F-12 and F-13. If an antibody was negative for rosette formation but absorbed onto the test antigen system it was deemed to be a positive reaction such that 1=reaction by absorption test is positive though gives a negative test for rosette formation 4=no reaction where only the absorption test was done;

5=positive reaction where only the absorption test was done.

i.e. 0 test for rosette formation is further tested by the absorption test. Therefore, 0 on this table indicates no reaction by either absorption or rosette formation only for mAbs R-7, F-15, F-16, F-17, F-18, and R-19.

Legend to Table II

Serological reaction of lung panel monoclonal antibodies with normal human cell lines. Tests same as for Table I.

Legend to Table III

Results of Table I are summarized for each of the lung mAbs with each type of normal or cancer cell line tested.

Legend to Table IV

Immunopathology reaction of lung panel monoclonal antibodies with fetal and adult normal human tissues in frozen section by indirect immunofluorescence.

0=no reaction

+=heterogeneous reaction within the tissue

++=homogeneous positive reaction within the tissue e.g. heterogeneous reaction is found with mAb J143 which reacts only with basal epithelial cells of normal urothelium. (J143 is a bladder mAb)

Legend to Table V

Immunopathological reaction of lung panel monoclonal antibodies with human cancer tissues in frozen sections by indirect immunofluorescence.

0=no reaction

+=positive reaction

++=very positive reaction

±=heterogeneous reaction

TABLE I

SEROLOGICAL REACTION OF MONOCLONAL ANTIBODIES WITH HUMAN TUMOR CELL LINES

| CELLS TESTED | F-7 | F-8 | F-10 | F-11 | F-15 | F-16 | F-17 | F-18 | F-19 | F-1 | F-2 | F-3 | F-5 | F-12 | F-13 | F-4 |
|---|---|---|---|---|---|---|---|---|---|---|---|---|---|---|---|---|
| Ig class | $\gamma 1$ | $\gamma 1$ | $\gamma 1$ | $\gamma 2b$ | $\gamma 1$ | $\gamma 1$ | $\gamma 1$ | $\gamma 1$ | $\gamma 1$ | M | M | M | M | M | M | M |
| Antigen detected | 48 + 180K | 90K | 32/47K | | 44K | 90K | 95K | | 85/135K | | | | | | | |
| Lung cancer: | | | | | | | | | | | | | | | | |
| SK-LC-1 | 0 | 3 | 3 | 0 | 1 | 0 | 2 | 0 | 0 | 0 | 0 | 3 | 0 | 0 | 0 | |
| -2 | 0 | 3 | 3 | 3 | 0 | 3 | 3 | 0 | 0 | 3 | 3 | 3 | 0 | 3 | 3 | |
| -3 | 0 | 0 | 3 | 2 | 2 | 0 | 2 | 0 | 0 | 2 | 0 | 0 | 0 | 0 | 0 | |
| -4 | 0 | 0 | 3 | 0 | 0 | 0 | 2 | 0 | 0 | 2 | 0 | 3 | 0 | 0 | 0 | |
| -5 | 0 | 3 | 3 | 2 | 0 | 2 | 1 | 0 | 0 | 0 | 0 | 2 | 0 | 0 | 0 | |
| -6 | 3 | 3 | 3 | 3 | 3 | 0 | 0 | 0 | 3 | 3 | 3 | 3 | 3 | 3 | 3 | 3 |
| -7 | 0 | 2 | 3 | 0 | 0 | 0 | 1 | 0 | 0 | 0 | 2 | 0 | 2 | 0 | 0 | |
| -8 | 0 | 3 | 3 | 2 | 3 | 3 | 3 | 3 | 0 | 3 | 0 | 2 | 0 | 0 | 2 | |
| -9 | 0 | 3 | 3 | 0 | 0 | 2 | 2 | 0 | 0 | 2 | 0 | 3 | 0 | 0 | 2 | |
| -10 | 0 | 2 | 3 | 0 | 3 | 0 | 2 | 0 | 0 | 2 | 0 | 0 | 0 | 0 | 3 | |
| -11 | 0 | 0 | 3 | 0 | 1 | 0 | 1 | 0 | 0 | 0 | 0 | 2 | 0 | 0 | 0 | |
| -12 | 0 | 2 | 3 | 0 | 1 | 0 | 2 | 0 | 0 | 0 | 0 | 2 | 0 | 0 | 0 | |
| -13 | 0 | 3 | 3 | 3 | 1 | 3 | 3 | 0 | 2 | 2 | 0 | 3 | 0 | 0 | 2 | |
| -14 | 3 | 3 | 3 | 3 | 0 | 3 | 2 | 0 | 0 | 2 | 0 | 0 | 0 | 0 | 2 | |
| -15 | 0 | 0 | 0 | 0 | 0 | 0 | 2 | 0 | 0 | 2 | 3 | 2 | 2 | 0 | 0 | |
| -16 | 0 | 0 | 3 | 0 | 0 | 0 | 3 | 0 | 0 | 2 | 0 | 2 | 0 | 3 | 2 | |

TABLE I-continued

SEROLOGICAL REACTION OF MONOCLONAL ANTIBODIES WITH HUMAN TUMOR CELL LINES

| | F-7 | F-8 | F-10 | F-11 | F-15 | F-16 | F-17 | F-18 | F-19 | F-1 | F-2 | F-3 | F-5 | F-12 | F-13 | F-4 |
|---|---|---|---|---|---|---|---|---|---|---|---|---|---|---|---|---|
| Ig class of antibody | γ1 | γ1 | γ1 | γ2b | γ1 | γ1 | γ1 | γ1 | γ1 | M | M | M | M | M | M | M |
| Antigen detected | 48 + 180K | 90K | 32/47K | | 44K | 90K | 95K | | 85/135K | | | | | | | |
| CELLS TESTED | | | | | | | | | | | | | | | | |
| SK-LC-LL | 0 | 0 | 2 | 0 | 1 | 0 | 2 | 0 | 0 | 2 | 0 | 0 | 0 | 0 | 0 | |
| SK-Mes-1 | 0 | 0 | 3 | 0 | 2 | 2 | 2 | 0 | 0 | 0 | 0 | 0 | 0 | 0 | 0 | |
| CaLu-1 | 0 | 3 | 3 | 0 | 0 | 0 | 3 | 0 | 3 | 2 | 0 | 0 | 0 | 0 | 0 | |
| Calu-4 | 0 | 3 | 3 | 0 | 0 | 0 | 3 | 0 | 3 | 2 | 0 | 0 | 0 | 0 | 0 | |
| SW 900 | 0 | 3 | 3 | 0 | 0 | 2 | 3 | 0 | 0 | 1 | 0 | 2 | 0 | 0 | 3 | |
| SW 1271 | 0 | 3 | 3 | 0 | 0 | 0 | 0 | 0 | 0 | 2 | 0 | 0 | 0 | 0 | | |
| BREAST CA: | | | | | | | | | | | | | | | | |
| ALAB | 0 | 3 | 3 | 0 | 0 | 3 | 0 | 0 | 0 | 0 | 0 | 3 | 0 | 0 | 0 | |
| MCF-7 | 0 | 3 | 3 | 0 | 1 | 0 | 1 | 0 | 0 | 3 | 3 | 3 | 0 | 3 | 3 | |
| BT-20 | 0 | 3 | 3 | 0 | 0 | 0 | 0 | 0 | 0 | 2 | 0 | 2 | 0 | 0 | 2 | |
| CaMa | 0 | 3 | 3 | 2 | 3 | 3 | 2 | 0 | 0 | 3 | 2 | 3 | 0 | 3 | 3 | |
| RENAL CA | | | | | | | | | | | | | | | | |
| SK-RC-4 | 2 | 3 | 3 | 2 | 3 | 3 | 3 | 0 | 0 | 1 | 0 | 0 | 0 | | 3 | |
| SK-RC-6 | 0 | 3 | 3 | 2 | 3 | 0 | 3 | 0 | 0 | 3 | 0 | 0 | 0 | 0 | 2 | |
| SK-RC-7 | 3 | 3 | 3 | 3 | 3 | 3 | 3 | 0 | 0 | 3 | 0 | 2 | 0 | 0 | 2 | |
| SK-RC-28 | 0 | 3 | 3 | 2 | 3 | 3 | 3 | 0 | 0 | 3 | 0 | 0 | 0 | 0 | 0 | |
| BLADDER CA | | | | | | | | | | | | | | | | |
| RT-4 | 0 | 0 | 2 | 0 | 0 | 0 | 1 | 0 | 0 | 2 | 0 | 2 | 0 | 0 | 0 | |
| 5637 | 0 | 3 | 3 | 0 | 0 | 0 | 1 | 0 | 0 | 2 | 0 | 2 | 0 | 0 | 0 | |
| T-24 | 1 | 0 | 3 | 0 | 0 | 0 | 3 | 0 | 0 | 2 | 0 | 3 | 0 | 0 | 3 | |
| TCCSUP | 1 | | | | 2 | 0 | 0 | 0 | 1 | 2 | 0 | 3 | 0 | 0 | 3 | |
| Scaber | 0 | | | | 0 | 0 | 1 | 0 | 0 | 0 | 0 | 2 | 0 | 0 | 0 | |
| COLON CA | | | | | | | | | | | | | | | | |
| HT-29 | 0 | 3 | 3 | 0 | 3 | 0 | 0 | 0 | 0 | 0 | 0 | 0 | 0 | 0 | 0 | |
| SW-837 | 0 | 0 | 0 | 0 | 0 | 0 | 1 | 0 | 0 | 0 | 0 | 3 | 0 | 0 | 0 | |
| SW-1083 | 0 | 0 | 0 | 0 | 0 | 0 | 1 | 0 | 0 | 0 | 0 | 3 | 0 | 0 | 0 | |
| SW-116 | 0 | 3 | 3 | 0 | 2 | 0 | 0 | 0 | 0 | 0 | 0 | 3 | 0 | 0 | 0 | |
| SW-1222 | 0 | 0 | 3 | 0 | 3 | 0 | 1 | 0 | 0 | 0 | 0 | 0 | 0 | 0 | 0 | |
| ASTROCYTOMAS | | | | | | | | | | | | | | | | |
| SK-MG-1 | 0 | 2 | 3 | 2 | 1 | 0 | 0 | 0 | 3 | 0 | 0 | 0 | 0 | 0 | 0 | |
| 2 | 0 | 3 | 3 | 2 | 0 | 0 | 3 | 0 | 3 | 3 | | 0 | 0 | 0 | 0 | |
| 5 | 0 | 3 | 3 | 2 | 2 | 2 | 0 | 0 | 3 | | | 0 | | | | |
| 10 | 0 | 3 | 3 | 2 | 1 | 2 | 0 | 0 | 3 | 0 | 0 | 0 | 0 | 0 | | |
| 12 | 0 | 3 | 3 | 3 | 0 | 0 | 0 | 0 | 3 | 2 | 0 | 0 | 0 | 0 | 3 | |
| 13 | 0 | 0 | 3 | 2 | 0 | 0 | 0 | 0 | 3 | 0 | 0 | 0 | 0 | 0 | 2 | |
| T-98 | 0 | 0 | 3 | 0 | 1 | 0 | 0 | 0 | 0 | 0 | 0 | 0 | 0 | 0 | 0 | |
| U 251 | 0 | 3 | 3 | 3 | 0 | 3 | 0 | 0 | 0 | 0 | 0 | 0 | 0 | 0 | 2 | |
| Scanti | 0 | 3 | 3 | 3 | 0 | 0 | 0 | 0 | 3 | 2 | 0 | 0 | 0 | 0 | 0 | |
| MELANOMAS | | | | | | | | | | | | | | | | |
| SK-MEL 28 | 0 | 0 | 2 | 0 | 0 | 0 | 0 | 0 | 0 | 0 | 0 | 0 | 0 | 0 | 2 | |
| SK-MEL 33 | 0 | 2 | 0 | 0 | 0 | 0 | 0 | 0 | 0 | 0 | 0 | 0 | 0 | 0 | 0 | |
| SK-MEL 37 | 0 | 3 | 3 | 0 | 0 | 0 | 0 | 0 | 0 | 0 | 0 | 0 | 0 | 0 | 0 | |
| SK-MEL 13 | 0 | | | 2 | 0 | 0 | 0 | 0 | 0 | 0 | 0 | 0 | 0 | 0 | 0 | |
| SK-MEL 85 | 0 | 3 | 3 | 3 | 0 | 0 | 0 | 0 | 3 | 0 | 0 | 0 | 0 | 0 | 0 | |
| SK-MEL 41 | 0 | 0 | 3 | 0 | 0 | 0 | 2 | 0 | 3 | 0 | 0 | 0 | 0 | 0 | 0 | |
| SK-MEL 42 | 0 | 0 | 3 | 2 | 0 | 0 | 2 | 0 | 3 | 0 | 0 | 0 | 0 | 0 | 2 | |
| SK-MEL 29 | 0 | 0 | 3 | 2 | 0 | 0 | 0 | 0 | 1 | 0 | 0 | 0 | 0 | 0 | 0 | |
| OVARIAN & UTERUS CA | | | | | | | | | | | | | | | | |
| ME-180 | 0 | 3 | 3 | 0 | 0 | 0 | 1 | 1 | 0 | 3 | 0 | 3 | 0 | | 3 | |
| Schustack | 0 | 0 | 2 | 0 | 0 | 0 | 1 | 0 | 0 | 2 | 0 | 3 | 0 | 0 | 0 | |
| Turanek | | | | | 1 | 0 | 1 | 0 | 0 | 3 | 0 | 3 | 0 | | | |
| OV-3 | 0 | 0 | 2 | 0 | 1 | 0 | 2 | 0 | 0 | 0 | 0 | | 0 | 0 | 0 | |
| OV-2774 | 0 | | | | 0 | 3 | 3 | 0 | 0 | 2 | 0 | | 0 | 0 | 0 | |
| SW-626 | 0 | | | 0 | 0 | 0 | 1 | 0 | 0 | 2 | 0 | 3 | 0 | 0 | 3 | |
| Leukemias | 4 | | | | 4 | 4 | 4 | 4 | 4 | | | | | | | |
| Molt 4 | 4 | | | | 4 | 4 | 4 | 4 | 4 | | | | | | | |
| T-45 | 4 | | | | 4 | 4 | 4 | 4 | 4 | | | | | | | |
| BALL 1 | 4 | | | | 4 | 4 | 4 | 4 | 4 | | | | | | | |
| Daud 1 | 4 | | | | 4 | 4 | 4 | 4 | 4 | | | | | | | |
| HL-60 | 4 | | | | 4 | 4 | 4 | 4 | 4 | | | | | | | |
| K-562 | 5 | | | | 4 | 4 | 5 | 4 | 4 | | | | | | | |
| KG-1 | 5 | | | | 4 | | | 4 | 4 | | | | | | | |
| B-Cells (EBV) | | | | | | | | | | | | | | | | |
| DX | 4 | | | | 4 | 4 | | 4 | 4 | | | | | | | |
| BD | 4 | | | | 4 | 4 | | 4 | | | | | | | | |

TABLE II

SEROLOGICAL REACTION OF LUNG MONOCLONAL ANTIBODIES WITH NORMAL HUMAN CELL LINES

ANTIBODY

| CELLS TESTED | F-7 | F-8 | F-10 | F-11 | F-15 | F-16 | F-17 | F-18 | F-19 | F-1 | F-2 | F-3 | F-5 | F-12 | F-13 |
|---|---|---|---|---|---|---|---|---|---|---|---|---|---|---|---|
| Adult Fibroblasts | | | | | | | | | | | | | | | |
| Skin G. | 0 | 0 | 3 | 0 | 0 | 0 | 0 | 0 | | 0 | | 0 | | | |
| Skin B. | 0 | 0 | 3 | 0 | 0 | 0 | 0 | 0 | 3 | 0 | | 0 | | | |
| Lung Cot. | 0 | 3 | 3 | 0 | 0 | 0 | 0 | 0 | 3 | 0 | | 0 | 0 | | 0 |
| Lung Va | 0 | 3 | 3 | 2 | 0 | 0 | 0 | 0 | 3 | 0 | 0 | 0 | 0 | 0 | 0 |
| Lung Lu | 0 | 0 | 3 | 3 | | 0 | 0 | 0 | 3 | 0 | | 0 | 0 | | 0 |
| Lung Bu | 0 | 2 | 3 | 2 | 0 | 0 | 0 | 0 | 3 | 0 | 0 | 0 | 0 | 0 | 0 |
| Lung Ka | 0 | 0 | 3 | 0 | 0 | 0 | 0 | | 3 | 0 | | 0 | 0 | | 0 |
| Lung Ba | 0 | | | | 0 | 0 | 0 | 0 | 3 | 0 | 0 | 0 | 0 | 0 | 0 |
| Lung Pa | 0 | 2 | 3 | 0 | 0 | 0 | 0 | 0 | | | | | | | |
| Lung Co | 0 | 3 | | | 0 | 0 | | 0 | | | | | | | |
| Fetal Lung Fibroblasts 0 | 3 | 3 | 2 | 0 | 2 | 2 | 0 | 3 | | | | | | | |
| Normal Kidney | 0 | 3 | 3 | 2 | 2 | 3 | 3 | 0 | 2 | 0 | | 0 | | | |

TABLE III

SUMMARY OF SEROLOGICAL REACTIONS OF LUNG MONOCLONAL ANTIBODIES WITH THE DIFFERENT NORMAL AND TUMOR CELL LINES

| CELLS TESTED Tissue Culture | F-7 | F-8 | F-10 | F-11 | F-15 | F-16 | F-17 | F-18 | F-19 | F-1 | F-2 | F-3 | F-5 | F-12 | F-13 |
|---|---|---|---|---|---|---|---|---|---|---|---|---|---|---|---|
| Breast Ca. | 0/4 | 4/4 | 4/4 | 1/4 | 2/4 | 2/4 | 2/4 | 0/4 | 0/4 | 3/4 | 2/4 | 4/4 | 0/4 | 2/4 | 3/4 |
| Colon Ca. | 0/5 | 2/5 | 3/5 | 0/5 | 3/5 | 3/5 | 0/5 | 0/5 | 0/5 | 0/5 | 0/5 | 3/5 | 0/5 | 0/5 | 0/5 |
| Renal Ca. | 2/4 | 4/4 | 4/4 | 4/4 | 4/4 | 3/4 | 4/4 | 0/4 | 0/4 | 3/4 | 0/4 | 1/4 | 0/4 | 0/2 | 3/4 |
| Bladder Ca. | 2/5 | 1/3 | 3/3 | 0/0 | 1/5 | 0/5 | 4/5 | 0/5 | 1/5 | 4/5 | 0/5 | 5/5 | 0/5 | 0/5 | 3/5 |
| Ovarian Ca. | 0/5 | 1/3 | 3/3 | 0/4 | 0/5 | 2/6 | 6/6 | 1/5 | 0/5 | 5/6 | 0/6 | 4/4 | 0/6 | 0/4 | 1/6 |
| Astrocytomas 0/9 | 7/9 | 9/9 | 8/9 | 4/9 | 3/9 | 1/9 | 0/9 | 7/8 | 3/6 | 0/7 | 0/8 | 0/8 | 0/8 | 3/7 | |
| Melanomas | 0/8 | 3/7 | 7/7 | 5/8 | 0/8 | 0/8 | 3/8 | 0/8 | 4/8 | 0/8 | 0/8 | 0/8 | 0/8 | 0/8 | 3/8 |
| Fibroblasts adult) | 0/10 | 5/9 | 8/8 | 3/8 | 0/9 | 0/9 | 0/9 | 0/9 | 7/7 | 0/8 | 0/3 | 0/8 | 0/6 | 0/3 | 0/6 |
| Fibroblasts (fetal) | 0/1 | 1/1 | 1/1 | 1/1 | 0/1 | 1/1 | 1/1 | 0/1 | 1/1 | 0/1 | | 0/1 | 0/1 | | 0/1 |
| Kidney (normal) | 0/1 | 1/1 | 1/1 | 1/1 | 1/1 | 1/1 | 1/1 | 0/1 | 1/1 | 0/1 | | 0/1 | | | |
| Lung cancer | 2/22 | 15/22 | 21/22 | 7/22 | 10/22 | 8/22 | 20/22 | 1/22 | 4/22 | 15/22 | 4/22 | 13/22 | 3/22 | 3/22 | 9/21 |

TABLE IV

NORMAL HUMAN TISSUE DISTRIBUTION OF THE MONOCLONAL ANTIBODIES OF THE LUNG PROJECT AS TESTED BY IMMUNOFLUORESCENCE

| ADULT TISSUES (Normal) | F-1 | F-2 | F-4 | F-5 | F-7 | F-9 | F-12 | F-18 |
|---|---|---|---|---|---|---|---|---|
| LUNG | 0 | 0 | 0 | + | 0 | + | 0 | 0 |
| Bronchial Epithelium | 0 | 0 | 0 | + | 0 | ± | 0 | 0 |
| Cartilage | 0 | 0 | 0 | 0 | 0 | 0 | 0 | 0 |
| Glandular Epithelium | 0 | 0 | 0 | + | 0 | + | 0 | 0 |
| Pneumocytes | 0 | 0 | 0 | 0 | 0 | 0 | 0 | 0 |
| Connect.Tis. | 0 | 0 | 0 | 0 | 0 | 0 | 0 | 0 |
| HEART (ms) | 0 | 0 | 0 | 0 | 0 | 0 | 0 | 0 |
| SPLEEN | 0 | 0 | 0 | ± | 0 | 0 | 0 | 0 |
| White pulp | 0 | 0 | 0 | ± | 0 | 0 | 0 | 0 |
| Red pulp | 0 | 0 | 0 | 0 | 0 | 0 | 0 | 0 |
| LIVER | 0 | 0 | 0 | 0 | 0 | + | 0 | 0 |
| Hepatocyte | 0 | 0 | 0 | 0 | 0 | 0 | 0 | 0 |
| Bil. Epit. | 0 | 0 | 0 | 0 | 0 | + | 0 | 0 |
| Sinusoids | 0 | 0 | 0 | ± | 0 | 0 | 0 | 0 |
| GALLBLADDER | 0 | 0 | 0 | 0 | 0 | + | 0 | 0 |
| ESOPHAGUS | 0 | 0 | 0 | ± | 0 | ± | 0 | 0 |
| STOMACH | 0 | 0 | 0 | + | 0 | + | 0 | 0 |
| SM.INTEST. | 0 | 0 | 0 | + | 0 | ± | 0 | 0 |
| COLON | 0 | 0 | 0 | + | 0 | ± | 0 | 0 |
| G.I. Smc | 0 | 0 | 0 | 0 | 0 | 0 | 0 | 0 |
| PANCREAS | 0 | 0 | 0 | + | 0 | + | 0 | 0 |
| Exocrine | 0 | 0 | 0 | ± | 0 | + | 0 | 0 |
| Endocrine | 0 | 0 | 0 | 0 | 0 | 0 | 0 | 0 |
| KIDNEY | 0 | 0 | 0 | + | 0 | + | 0 | 0 |
| Glomerulus | 0 | 0 | 0 | 0 | 0 | 0 | 0 | 0 |
| Prox. Tub. | 0 | 0 | 0 | + | 0 | 0 | 0 | 0 |
| Henle's L. | 0 | 0 | 0 | + | 0 | ± | 0 | 0 |
| Distal Tub. | 0 | 0 | 0 | + | 0 | + | 0 | 0 |
| Collec. Tub. | 0 | 0 | 0 | + | 0 | + | 0 | 0 |

TABLE IV-continued
NORMAL HUMAN TISSUE DISTRIBUTION OF THE MONOCLONAL ANTIBODIES OF THE LUNG PROJECT AS TESTED BY IMMUNOFLUORESCENCE

| ADULT TISSUES (Normal) | F-1 | F-2 | F-4 | F-5 | F-7 | F-9 | F-12 | F-18 |
|---|---|---|---|---|---|---|---|---|
| URETER | 0 | 0 | 0 | + | 0 | + | 0 | 0 |
| URI.BLAD. | 0 | 0 | 0 | + | 0 | + | 0 | 0 |
| ADRENAL | 0 | 0 | 0 | 0 | 0 | 0 | 0 | 0 |
| Cortex | 0 | 0 | 0 | 0 | 0 | 0 | 0 | 0 |
| Medulla | 0 | 0 | 0 | 0 | 0 | 0 | 0 | 0 |
| THYROID | 0 | 0 | 0 | + | 0 | 0 | 0 | 0 |
| Epithelium | 0 | 0 | 0 | ± | 0 | 0 | 0 | 0 |
| Colloid | 0 | 0 | 0 | 0 | 0 | 0 | 0 | 0 |
| BREAST | 0 | 0 | 0 | + | 0 | + | 0 | 0 |
| Duct Cells | 0 | 0 | 0 | + | 0 | ± | 0 | 0 |
| Acinar Cel. | 0 | 0 | 0 | + | 0 | ± | 0 | 0 |
| Connec. Tis. | 0 | 0 | 0 | 0 | 0 | 0 | 0 | 0 |
| PROSTATE | 0 | 0 | 0 | 0 | 0 | 0 | 0 | 0 |
| Epithelium | 0 | 0 | 0 | 0 | 0 | 0 | 0 | 0 |
| Stroma | 0 | 0 | 0 | 0 | 0 | 0 | 0 | 0 |
| TESTE | 0 | 0 | 0 | 0 | 0 | 0 | 0 | 0 |
| Germ Cells | 0 | 0 | 0 | 0 | 0 | 0 | 0 | 0 |
| Endocrine Cells | 0 | 0 | 0 | 0 | 0 | 0 | 0 | 0 |
| Connec.Tis. | 0 | 0 | 0 | 0 | 0 | 0 | 0 | 0 |
| OVARY | 0 | 0 | 0 | 0 | 0 | 0 | 0 | 0 |
| Germ Cells | 0 | 0 | 0 | 0 | 0 | 0 | 0 | 0 |
| Connec. Tis. | 0 | 0 | 0 | 0 | 0 | 0 | 0 | 0 |
| FALLOP. TUB. | 0 | 0 | 0 | 0 | 0 | 0 | 0 | 0 |
| UTERUS | 0 | 0 | 0 | ± | 0 | ± | 0 | 0 |
| Endometrium | 0 | 0 | 0 | ± | 0 | ± | 0 | 0 |
| Myometrium | 0 | 0 | 0 | 0 | 0 | 0 | 0 | 0 |
| CERVIX | 0 | 0 | 0 | 0 | 0 | 0 | 0 | 0 |
| Endocervix | 0 | 0 | 0 | 0 | 0 | 0 | 0 | 0 |
| Exocervix | 0 | 0 | 0 | 0 | 0 | 0 | 0 | 0 |
| PLACENTA | 0 | 0 | 0 | + | 0 | + | 0 | 0 |
| Cytotrophb. | 0 | 0 | 0 | + | 0 | + | 0 | 0 |
| Syncytotrb. | 0 | 0 | 0 | + | 0 | + | 0 | 0 |
| Sinusoids | 0 | 0 | 0 | 0 | 0 | 0 | 0 | 0 |
| SKIN | 0 | 0 | 0 | + | 0 | 0 | 0 | 0 |
| Epidermis | 0 | 0 | 0 | 0 | 0 | 0 | 0 | 0 |
| Melanocytes | 0 | 0 | 0 | 0 | 0 | 0 | 0 | 0 |
| Sweat Gld. | 0 | 0 | 0 | + | 0 | 0 | 0 | 0 |
| Sebaceous G. | 0 | 0 | 0 | 0 | 0 | 0 | 0 | 0 |
| Dermis CT | 0 | 0 | 0 | 0 | 0 | 0 | 0 | 0 |
| BRAIN | 0 | 0 | 0 | + | 0 | 0 | 0 | 0 |
| Neurons | 0 | 0 | 0 | ± | 0 | 0 | 0 | 0 |
| Glial Cell | 0 | 0 | 0 | ± | 0 | 0 | 0 | 0 |
| Dendrites | 0 | 0 | 0 | + | 0 | 0 | 0 | 0 |
| LYMPH NODE | 0 | 0 | 0 | 0 | 0 | 0 | 0 | 0 |
| Fol/Medul. | 0 | 0 | 0 | 0 | 0 | 0 | 0 | 0 |
| BLOOD VES. | 0 | 0 | 0 | 0 | 0 | 0 | 0 | 0 |
| Endothelium | 0 | 0 | 0 | 0 | 0 | 0 | 0 | 0 |
| Smooth Ms. | 0 | 0 | 0 | 0 | 0 | 0 | 0 | 0 |
| CAPILLARIES | 0 | 0 | 0 | 0 | 0 | 0 | 0 | 0 |
| SKELETAL MS | 0 | 0 | 0 | 0 | 0 | 0 | 0 | 0 |
| SOFT TISSUE | 0 | 0 | 0 | 0 | 0 | 0 | 0 | 0 |
| SECRETIONS | 0 | 0 | 0 | + | 0 | + | 0 | 0 |

TABLE V
HUMAN TUMOR TISSUE DISTRIBUTION OF THE MONOCLONAL ANTIBODIES OF THE LUNG AS TESTED BY IMMUNOFLUORESCENCE

| PATIENT | F-1 | F-2 | F-4 | F-5 | F-7 | F-9 | F-12 | F-18 |
|---|---|---|---|---|---|---|---|---|
| A. LUNG TUMORS/ADENO-CARCINOMAS | | | | | | | | |
| Me. | ++ | 0 | ++ | ± | 0 | 0 | 0 | 0 |
| Kr. | 0 | 0 | ± | ± | 0 | ± | 0 | 0 |
| Pa. | 0 | 0 | | ++ | 0 | 0 | 0 | 0 |
| Ge. | ± | 0 | 0 | ± | 0 | 0 | 0 | 0 |
| Si. | 0 | 0 | 0 | ± | 0 | ++ | 0 | 0 |
| Am. | 0 | 0 | 0 | ± | 0 | ± | 0 | 0 |
| In. | | | | | | | | |
| Ne. | | | | | | | | |
| Mu. | | | | | | | | |
| My. | | | | | | | | |
| Ga. | 0 | 0 | 0 | ++ | | | 0 | |
| Sa. | 0 | ± | ++ | ± | 0 | 0 | 0 | 0 |
| Dr. | | | | | | | | |
| St. | | | | | | | | |
| Gr. | 0 | | | | | | | |
| A. LUNG TUMORS/EPIDERMOID CARCINOMAS | | | | | | | | |
| Bia. | 0 | 0 | 0 | ± | 0 | 0 | 0 | 0 |
| Dug. | ± | ± | 0 | ± | 0 | ± | 0 | 0 |
| Hef. | 0 | 0 | 0 | ± | 0 | 0 | 0 | 0 |
| Maz. | + | ++ | 0 | + | 0 | ± | 0 | 0 |
| Mas. | 0 | 0 | 0 | + | 0 | 0 | 0 | 0 |
| Gui. | 0 | 0 | ± | ± | 0 | | 0 | 0 |
| Mel. | ± | ± | 0 | ± | 0 | 0 | 0 | 0 |
| Ea. | 0 | 0 | 0 | ± | 0 | 0 | 0 | 0 |
| #83-337 | 0 | 0 | 0 | ± | 0 | ± | 0 | 0 |
| A. LUNG TUMORS/CARCINOIDS | | | | | | | | |
| #83-692 | 0 | 0 | 0 | 0 | 0 | 0 | 0 | 0 |
| B. TUMOR TISSUES/TERATO CARCINOMAS | | | | | | | | |
| #83-1881 | 0 | 0 | 0 | ± | 0 | + | 0 | 0 |

TABLE V-continued

HUMAN TUMOR TISSUE DISTRIBUTION OF THE MONOCLONAL ANTIBODIES OF THE LUNG AS TESTED BY IMMUNOFLUORESCENCE

| PATIENT | F-1 | F-2 | F-4 | F-5 | F-7 | F-9 | F-12 | F-18 |
|---|---|---|---|---|---|---|---|---|
| #82-19590 | 0 | 0 | 0 | ± | 0 | + | 0 | 0 |
| B. TUMOR TISSUES/BLADDER TUMORS TRANSITIONAL CARCINOMAS | | | | | | | | |
| Caur. | 0 | 0 | 0 | ++ | 0 | 0 | 0 | 0 |
| Wil. | 0 | 0 | 0 | ± | 0 | ± | 0 | 0 |
| #83-20793 | 0 | 0 | 0 | ± | 0 | 0 | 0 | 0 |
| Gra. | 0 | 0 | 0 | ± | 0 | 0 | 0 | 0 |
| PAPILLOMAS | | | | | | | | |
| O'Sul | 0 | 0 | 0 | ++ | 0 | ± | | |
| B. TUMOR TISSUES/MELANOMAS PRIM. MEL. | | | | | | | | |
| #82-23 735 | 0 | 0 | 0 | 0 | 0 | 0 | 0 | 0 |
| MET. MEL. | | | | | | | | |
| 2-3-83 | 0 | 0 | 0 | 0 | 0 | 0 | 0 | 0 |

What is claimed is:

1. A method for differentiating between normal and malignant human lung cells which comprises contacting a human lung cell specimen with a panel of monoclonal antibodies and detecting malignant lung cells reacting immunologically with the monoclonal antibodies, wherein the panel comprises at least two monoclonal antibodies produced by hybridoma cell lines selected from the group consisting of F-1 (HB 8230), F-2 (HB 8253), F-3 (HB 8254), F-4 (HB 8255), F-5 (HB 8256), F-7 (HB 8258), F-8 (HB 8259), F-9 (HB 8260), F-10 (HB 8261), F-11 (HB 8262), F-12 (HB 8263), F-13 (HB 8264), F-15 (HB 8265), F-16 (HB 8266), F-17 (HB 8267), F-18 (HB 8268), and F-19 (HB 8269).

2. A method of claim 1 wherein the human lung cell specimen is separately or serially contacted with each antibody of the panel.

3. A method for differentiating benign lung tumor cells and malignant lung tumor cells which comprises contacting a human lung cell specimen with a panel of monoclonal antibodies and detecting malignant or benign lung tumor cells reacting immunologically with the monoclonal antibodies, wherein the panel comprises at least two monoclonal antibodies produced by hybridoma cell lines selected from the group consisting of F-1 (HB 8230), F-2 (HB 8253), F-3 (HB 8254), F-4 (HB 8255), F-5 (HB 8256), F-7 (HB 8258), F-8 (HB 8259), F-9 (HB 8260), F-10 (HB 8261), F-11 (HB 8262), F-12 (HB 8263), F-13 (HB 8264), F-15 (HB 8265), F-16 (HB 8266), F-17 (HB 8267), F-18 (HB 8268), and F-19 (HB 8269).

4. A method of claim 3 wherein the human lung cell specimen is separately or serially contacted with each antibody of the panel.

* * * * *